United States Patent
Um et al.

(10) Patent No.: US 10,065,983 B2
(45) Date of Patent: Sep. 4, 2018

(54) METHOD OF PREPARING BASE SEQUENCE OF 5'-COHESIVE END FOR SYNTHESIZING BRANCHED NUCLEIC ACID NANOSTRUCTURE

(71) Applicant: RESEARCH & BUSINESS FOUNDATION SUNGKYUNKWAN UNIVERSITY, Suwon-si (KR)

(72) Inventors: Soong Ho Um, Seoul (KR); In Hyun Song, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 638 days.

(21) Appl. No.: 14/672,700

(22) Filed: Mar. 30, 2015

(65) Prior Publication Data

US 2015/0274768 A1    Oct. 1, 2015

(30) Foreign Application Priority Data

Apr. 1, 2014    (KR) .......................... 10-2014-0038585

(51) Int. Cl.

| | | |
|---|---|---|
| *C07H 21/04* | (2006.01) | |
| *C12Q 1/68* | (2018.01) | |
| *C12P 19/34* | (2006.01) | |
| *B82Y 5/00* | (2011.01) | |
| *C12Q 1/6811* | (2018.01) | |

(52) U.S. Cl.
CPC ............... *C07H 21/04* (2013.01); *B82Y 5/00* (2013.01); *C12P 19/34* (2013.01); *C12Q 1/68* (2013.01); *C12Q 1/6811* (2013.01)

(58) Field of Classification Search
CPC .................................. C07H 21/04; B82Y 5/00
See application file for complete search history.

(56) References Cited

PUBLICATIONS

Um et al. (Nature Protocols. 2006; 1(2): 995-1000) (Year: 2006).*
Li et al. (Nature Materials. Jan. 2004; 3:38-42) (Year: 2004).*
Promega (Certificate of Analysis for T4 DNA Ligase/Part# 9PIM180) [2018] (Year: 2018).*
Aboul-Ela, Fareed, et al. "Base-base mismatches. Thermodynamics of double helix formation for dCA3XA3G+dCT3YT3G (X, Y=A, C, G, D)." Nucleic Acids Research. vol. 13. No. 13. (1985): 4811-4824.
Breslauer, Kenneth J., et al. "Predicting DNA duples stability from the base sequence." Proceedings of the National Academy of Sciences vol. 83 No. 11 (Jun. 1986): 3746-3750.
Cho, Younghyun, et al. "Controlled release of an anti-cancer drug from DNA structured nano-films." Scientific Reports 4:4078 (Feb. 12, 2014) (5 pages, in English).
Korean Office Action dated in counterpart Korean Application No. 10-2014-0038585 (4 pages in Korean).

* cited by examiner

*Primary Examiner* — Scott Long
(74) *Attorney, Agent, or Firm* — NSIP Law

(57) ABSTRACT

A method of preparing a base sequence for synthesis of a nucleic acid nanostructure, a method of synthesizing a nucleic acid nanostructure, a candidate base sequence pair, and a nucleic acid nanostructure are provided. A method of preparing a base sequence includes selecting candidate groups of base sequences of 5'-cohesive end having at least 50% GC content, calculating Gibb's free energy values of the selected candidate groups to re-select the candidate groups, and selecting the candidate groups, that have a sequence of 3 different successive bases among the base sequences from the re-selected candidate groups.

11 Claims, 9 Drawing Sheets

Specification includes a Sequence Listing.

[Fig. 1]
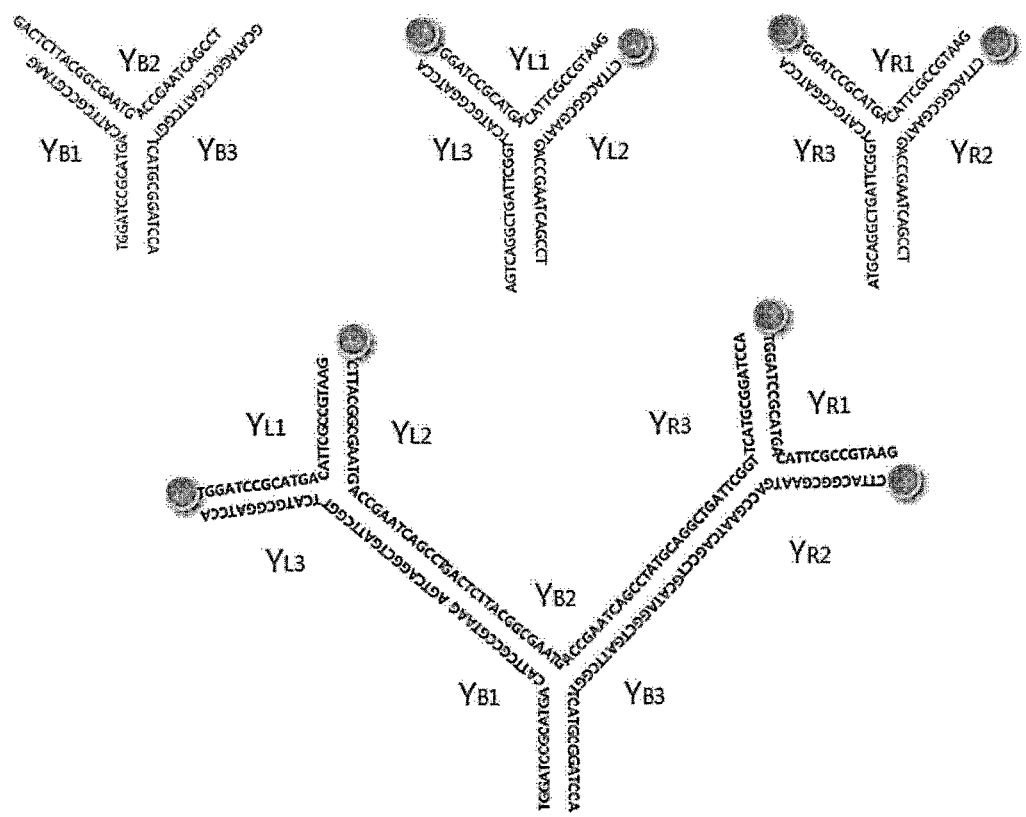

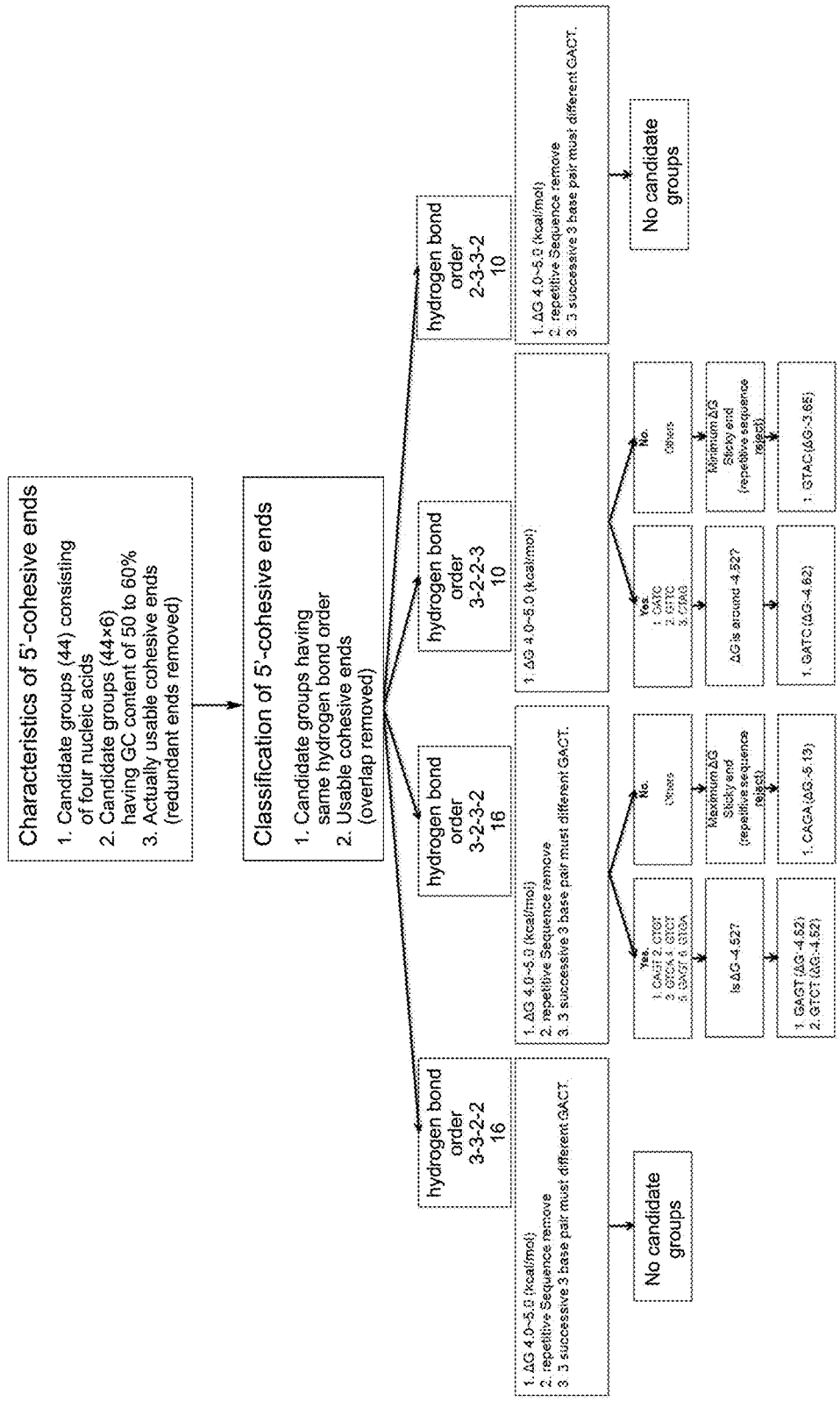
[Fig. 2]

[Fig. 3]
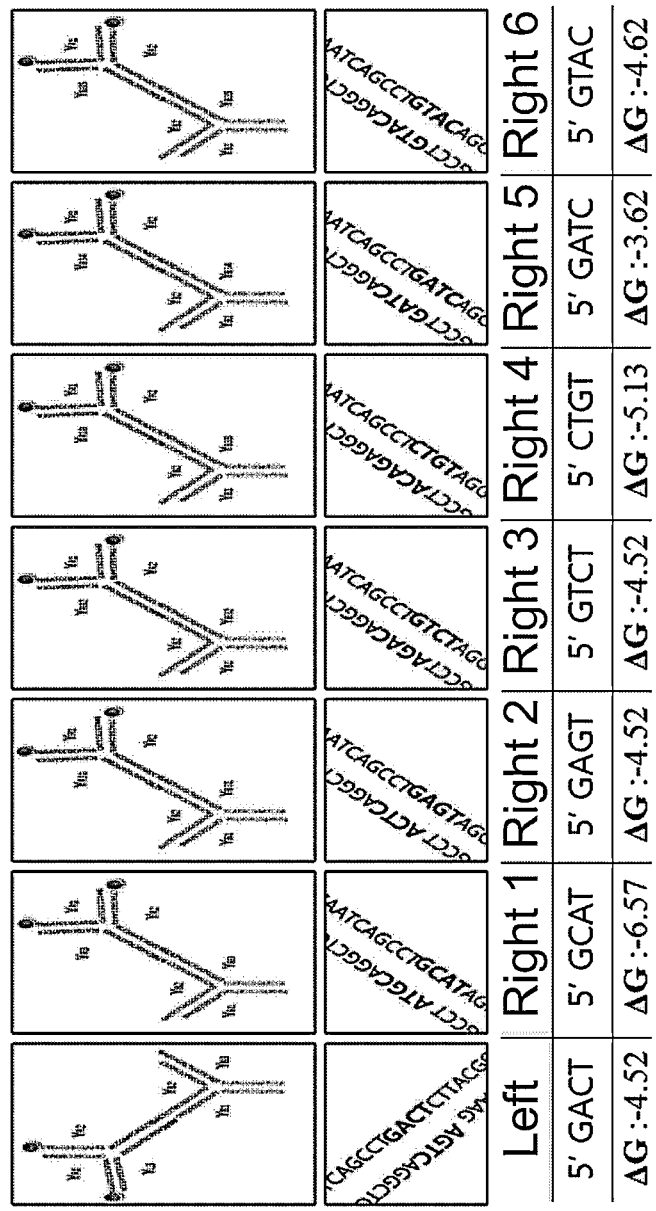

[Fig. 4]
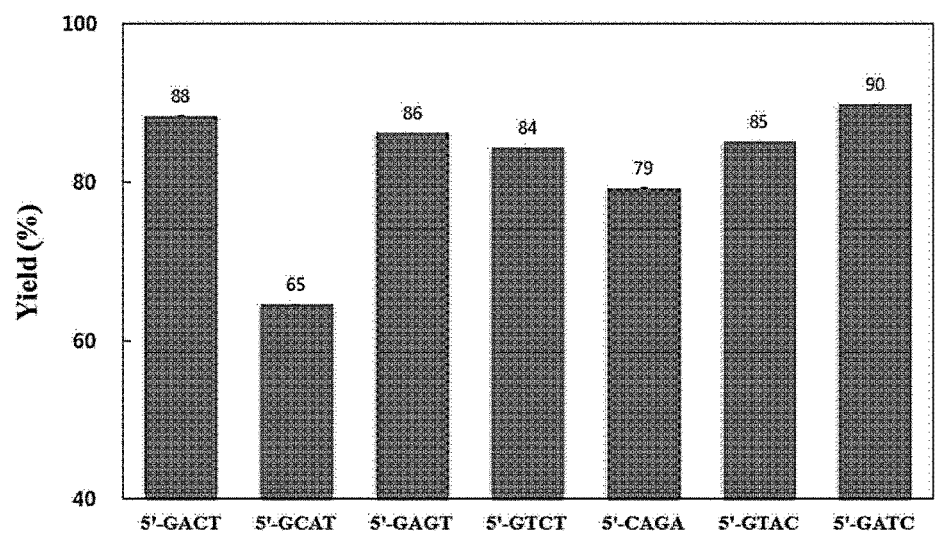

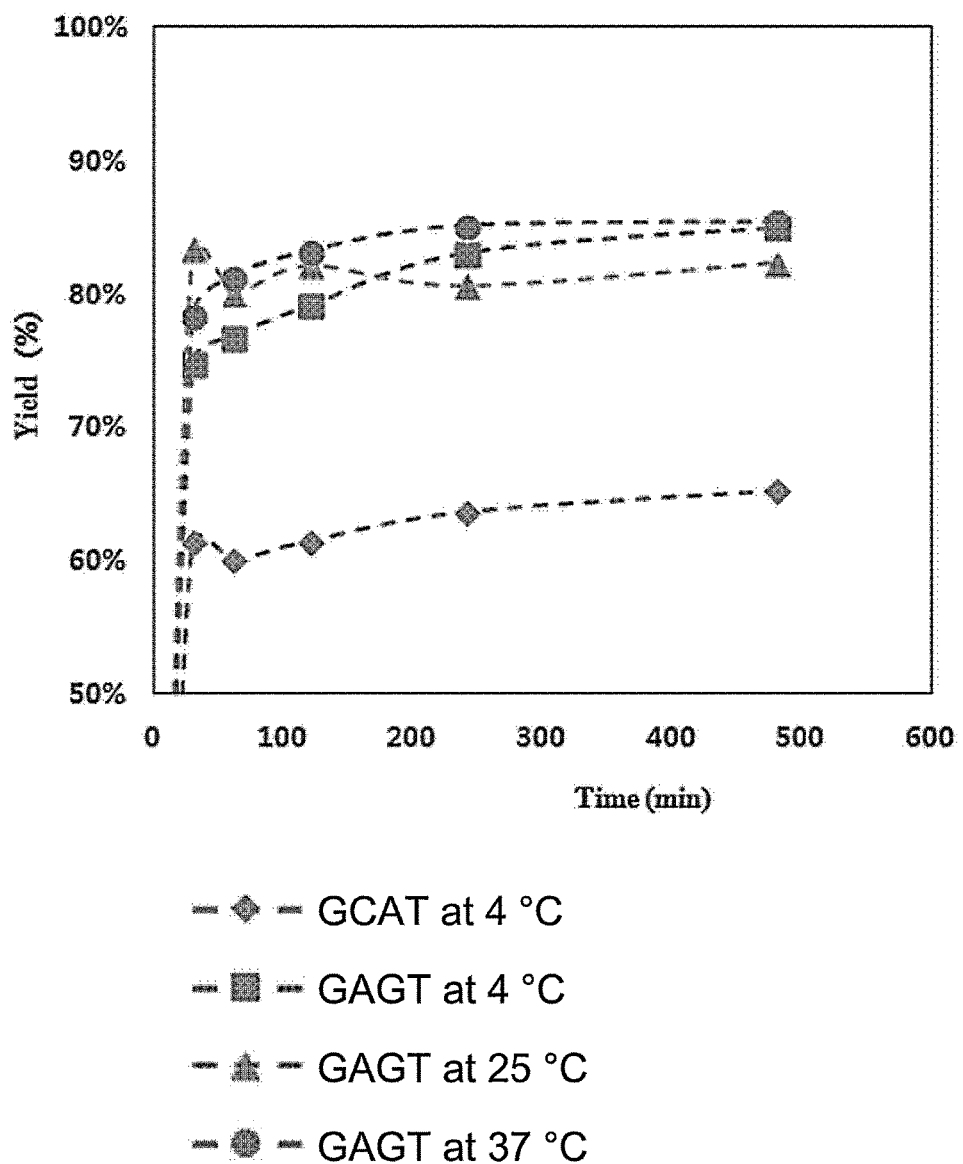

[Fig. 6A]
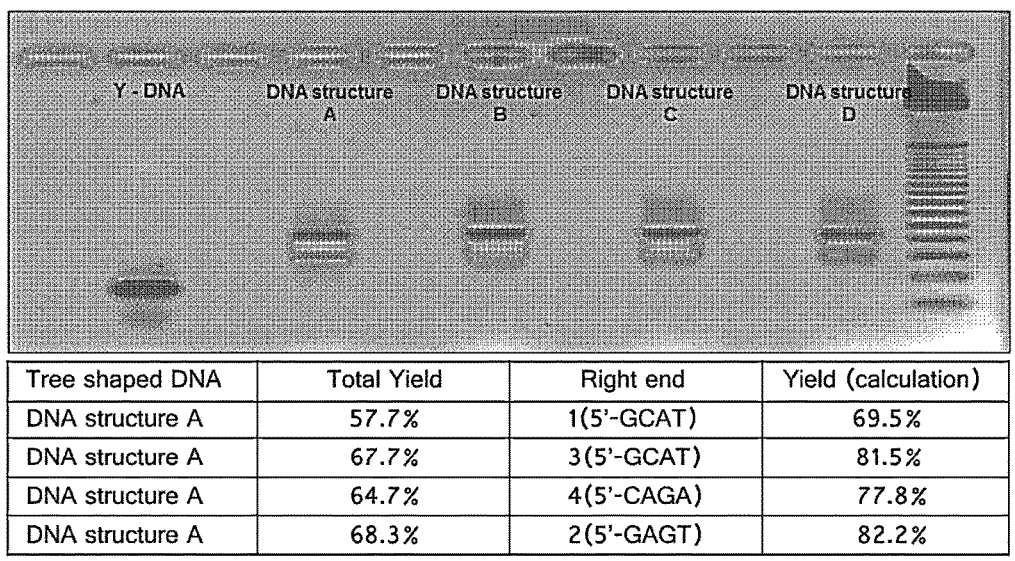
| Tree shaped DNA | Total Yield | Right end | Yield (calculation) |
|---|---|---|---|
| DNA structure A | 57.7% | 1(5'-GCAT) | 69.5% |
| DNA structure A | 67.7% | 3(5'-GCAT) | 81.5% |
| DNA structure A | 64.7% | 4(5'-CAGA) | 77.8% |
| DNA structure A | 68.3% | 2(5'-GAGT) | 82.2% |
Total yield = (Left yield) * (Right yield)
Left cohesive end (5'GACT)
Yield of left side : 83%

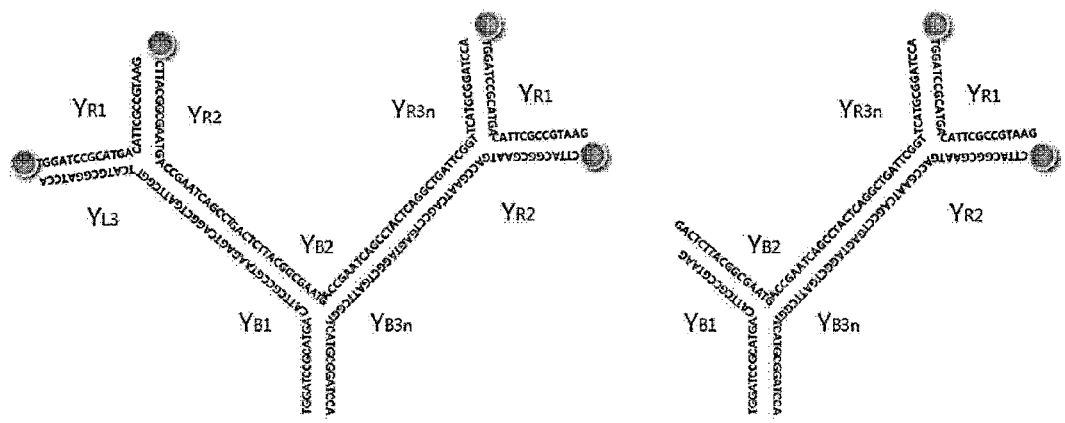
[Fig. 6B]

[Fig. 7A]

| Helix state | Mismatch (A) | Mismatch (B) | Mismatch (C) | Mismatch (D) |
|---|---|---|---|---|
| Sequence | 5'-GACT<br>3'-CTCA | 5'-GAGT<br>3'-CTGA | 5'-GACT<br>3'-CAGA | 5'-GTCT<br>3'-CTGA |
| Watson - Crick Base pair | Three | Three | Three | Three |
| Non Watson - Crick Base Pair | One | One | One | One |

[Fig. 7B]

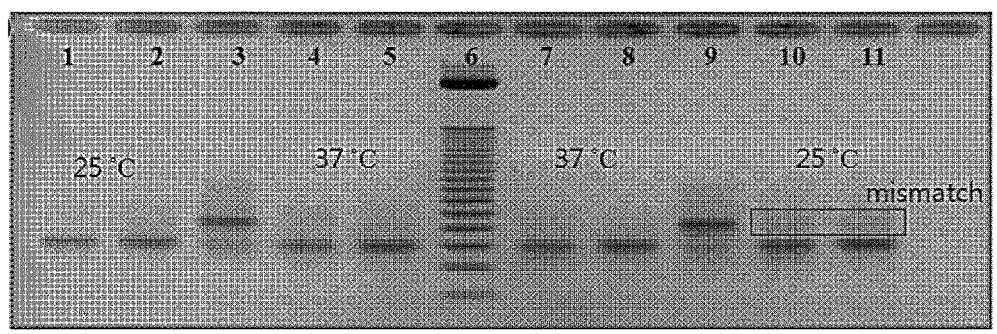

- L1, L2: MismatchA, MismatchB (25°C),
- L3: branched DNA
- L4, L5: MismatchA, MismatchB (37°C)
- L6: 50bp Ladder
- L7, L8: MismatchC, MismatchD (37°C),
- L9: branched DNA
- L10, L11: MismatchC, Mismatch D (25°C)

[Fig. 7C]
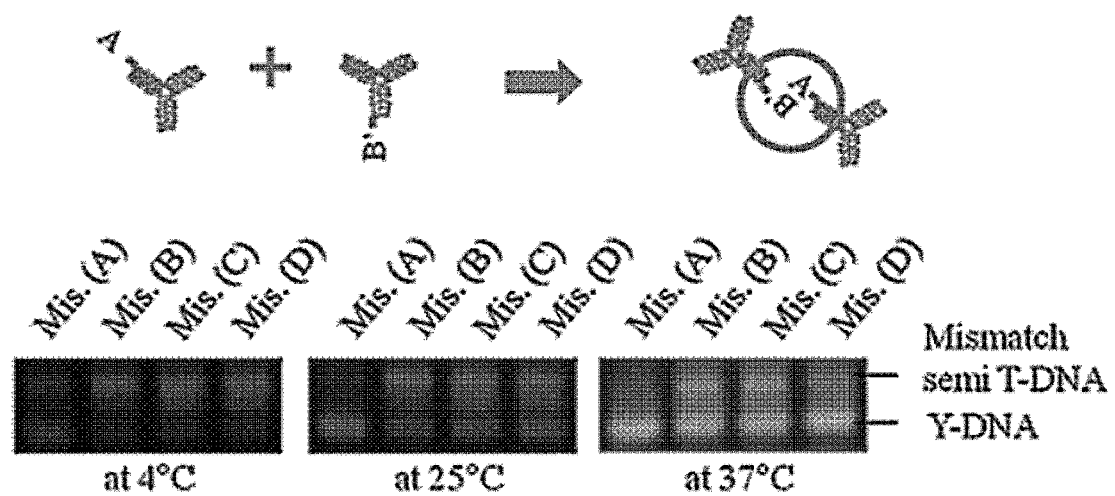

SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: YB1
<220> FEATURE:
<221> NAME/KEY: misc_binding
<222> LOCATION: (1)..(1)
<223> OTHER INFORMATION: biotin

<400> SEQUENCE: 1
tggatccgca tgacattcgc cgtaag

<210> SEQ ID NO 2
<211> LENGTH: 30
<212> TYPE: DNA
<213> ORGANISM: Artificial Sequence
<220> FEATURE:
<223> OTHER INFORMATION: YB2
<220> FEATURE:
<221> NAME/KEY: misc_binding
<222> LOCATION: (1)..(1)
<223> OTHER INFORMATION: Phosphorylation

<400> SEQUENCE: 2
gactcttacg gcgaatgacc gaatcagcct         30

<210> SEQ ID NO 3
<211> LENGTH: 30
<212> TYPE: DNA
<213> ORGANISM: Artificial Sequence
<220> FEATURE:
<223> OTHER INFORMATION: YB3
<220> FEATURE:
<221> NAME/KEY: misc_binding
<222> LOCATION: (1)..(1)
<223> OTHER INFORMATION: Phosphorylation

<400> SEQUENCE: 3
gcataggctg attcggttca tgcggatcca         30

<210> SEQ ID NO 4
<211> LENGTH: 26
<212> TYPE: DNA
<213> ORGANISM: Artificial Sequence
<220> FEATURE:
<223> OTHER INFORMATION: YL1
<220> FEATURE:
<221> NAME/KEY: misc_binding
<222> LOCATION: (1)..(1)
<223> OTHER INFORMATION: FAM(dye)

<400> SEQUENCE: 4
tggatccgca tgacattcgc cgtaag         26

<210> SEQ ID NO 5
<211> LENGTH: 26
<212> TYPE: DNA
<213> ORGANISM: Artificial Sequence
<220> FEATURE:
<223> OTHER INFORMATION: YL2
<220> FEATURE:
<221> NAME/KEY: misc_binding
<222> LOCATION: (1)..(1)
<223> OTHER INFORMATION: FAM(dye)

<400> SEQUENCE: 5
cttacggcga atgaccgaat cagcct         26

<210> SEQ ID NO 6
<211> LENGTH: 30
<212> TYPE: DNA
<213> ORGANISM: Artificial Sequence
<220> FEATURE:
<223> OTHER INFORMATION: YL3
<220> FEATURE:
<221> NAME/KEY: misc_binding
<222> LOCATION: (1)..(1)
<223> OTHER INFORMATION: Phosphorylation

<400> SEQUENCE: 6

```
agtcaggctg attcggttca tgcggatcca                                    30

<210> SEQ ID NO 7
<211> LENGTH: 26
<212> TYPE: DNA
<213> ORGANISM: Artificial Sequence
<220> FEATURE:
<223> OTHER INFORMATION: YR1
<220> FEATURE:
<221> NAME/KEY: misc_binding
<222> LOCATION: (1)..(1)
<223> OTHER INFORMATION: Cy5(dye)

<400> SEQUENCE: 7
tggatccgca tgacattcgc cgtaag                                        26

<210> SEQ ID NO 8
<211> LENGTH: 26
<212> TYPE: DNA
<213> ORGANISM: Artificial Sequence
<220> FEATURE:
<223> OTHER INFORMATION: YR2
<220> FEATURE:
<221> NAME/KEY: misc_binding
<222> LOCATION: (1)..(1)
<223> OTHER INFORMATION: Cy5(dye)

<400> SEQUENCE: 8
cttacggcga atgaccgaat cagcct                                        26

<210> SEQ ID NO 9
<211> LENGTH: 30
<212> TYPE: DNA
<213> ORGANISM: Artificial Sequence
<220> FEATURE:
<223> OTHER INFORMATION: YR3
<220> FEATURE:
<221> NAME/KEY: misc_binding
<222> LOCATION: (1)..(1)
<223> OTHER INFORMATION: Phosphorylation

<400> SEQUENCE: 9
agtcaggctg attcggttca tgcggatcca                                    30
```

METHOD OF PREPARING BASE SEQUENCE OF 5'-COHESIVE END FOR SYNTHESIZING BRANCHED NUCLEIC ACID NANOSTRUCTURE

STATEMENT REGARDING GOVERNMENT RIGHTS

This invention was made with government support of the Republic of Korea under Contract Nos. 2013016781 and 2013058670 awarded by Korean Ministry of Science, ICT and Future Planning. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 18, 2013, is named NewApplication_0420990022_SequenceListingCRT.txt.

CROSS-REFERENCE TO RELATED APPLICATION

This application claims the benefit under 35 U.S.C. § 119(a) of Korean Patent Application No. 10-2014-0038585, filed on Apr. 1, 2014 in the Korean Intellectual Property Office, the entire disclosure of which is incorporated herein by reference for all purposes.

BACKGROUND

1. Field

The present disclosure relates to a method of preparing a base sequence of 5'-cohesive end of a linear nucleic acid for synthesizing a Y-shaped nucleic acid nanostructure, and a method of synthesizing a dendrimer-like (branched) nucleic acid nanostructure using the Y-shaped nucleic acid nanostructure including the base sequence of cohesive end at the 5' terminus prepared by the method.

2. Description of Related Art

With the development of nucleic acid structural engineering, a variety of nucleic acid nanostructures have been designed and constructed. Spherical, dendrimer-like, rod-like, box-like, and even emoticon-like nucleic acid structures have been developed in addition to the conventional linear and circular natural nucleic acid structures. T4 ligation enzymes have been widely used to construct new structures in addition to the natural nucleic acid structures.

However, the use of the T4 ligation enzymes causes many problems regarding cohesive end ligation methods. For example, the product yield is low when T4 ligation enzymes are used, and the probability of errors in an expected target to be synthesized increases when ligations are performed using different 5'-cohesive ends.

For instance, it is difficult to synthesize a precise structure due to occurrence of mismatch ligations. In addition, when the synthesized nanostructure is used in vivo, severe side effects make it difficult to expect accurate results.

Accordingly, when a nucleic acid nanostructure is synthesized using a T4 ligation enzyme, it is necessary to verify a design of an additional base sequence of 5'-cohesive end and improve a ligation method so as to obtain a precise nucleic acid nanostructure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of preparing a base sequence of 5'-cohesive end of linear nucleic acids for synthesis of a nucleic acid nanostructure, the method involving: (a) selecting candidate groups of base sequences of 5'-cohesive end having guanine (G)-cytosine (C) content of 50 to 60%; (b) calculating Gibb's free energy values of the selected candidate groups of the step (a) to select candidates having maximum, median and minimum values, and performing ligation experiments on the candidates; (c) re-selecting the candidate groups having an approximation to the Gibb's free energy values of the candidates that are the most readily ligated based on the experimental results of step (b); and (d) selecting the candidate groups that have a sequence of 3 to 5 different successive bases among the base sequences from the re-selected candidate groups.

The method may be performed to reduce a probability of producing a mismatch ligation product upon synthesis of a dendrimer-like, X-shaped or T-shaped nucleic acid nanostructure.

According to another general aspect, there is provided a candidate group consisting of base sequences of 5'-cohesive end of linear nucleic acids prepared by the general aspect of the method described above in which number of the base is 4.

The candidate group may be selected from the group consisting of GAGT, GACT, GTCT, GTGT, GAGA, CTCT, GACA, GTGA, GTCA, CACT, CTGT, CAGT, CTAG, GATC, GTTC, CATC, and GATG.

According to another general aspect, there is provided candidate pair groups including two candidates that may be selected from the candidate group defined in the general aspect of candidate group described above, wherein the two candidates comprise a candidate pair group that is represented by 'o' in the following Table, the candidate pair group being used to synthesize a nucleic acid nanostructure.

TABLE

|  | GAGT | GACT | GTCT | GTGT | GAGA | CTCT | GACA | GTGA |
|---|---|---|---|---|---|---|---|---|
| GAGT | x | x | x | x | x | o | x | x |
| GACT | x | x | x | x | x | x | x | o |
| GTCT | x | x | x | x | o | x | o | x |
| GTGT | x | x | x | x | x | x | o | x |
| GAGA | x | x | o | x | x | o | x | x |
| CTCT | o | x | x | x | o | x | o | o |
| GACA | x | x | o | o | x | o | x | x |
| GTGA | x | o | x | x | x | o | x | x |
| GTCA | o | x | x | x | x | x | x | x |
| CACT | x | x | x | o | o | x | x | o |

TABLE-continued

|      | GAGT | GACT | GTCT | GTGT | GAGA | CTCT | GACA | GTGA |
|------|------|------|------|------|------|------|------|------|
| CTGT | o    | o    | x    | x    | o    | x    | o    | x    |
| CAGT | x    | x    | o    | x    | o    | x    | o    | o    |
| GTTC | o    | o    | x    | x    | o    | x    | o    | x    |
| CATC | o    | o    | o    | o    | o    | o    | o    | o    |
| GATG | x    | x    | o    | o    | x    | o    | x    | o    |

|      | GTCA | CACT | CTGT | CAGT | GTTC | CATC | GATG |
|------|------|------|------|------|------|------|------|
| GAGT | o    | x    | o    | x    | o    | o    | x    |
| GACT | x    | x    | o    | x    | o    | o    | x    |
| GTCT | x    | x    | x    | o    | x    | o    | o    |
| GTGT | x    | o    | x    | x    | x    | o    | o    |
| GAGA | x    | o    | o    | o    | o    | o    | x    |
| CTCT | x    | x    | x    | x    | x    | o    | o    |
| GACA | x    | x    | o    | o    | o    | o    | x    |
| GTGA | x    | o    | x    | o    | x    | o    | o    |
| GTCA | x    | o    | o    | o    | x    | o    | o    |
| CACT | o    | x    | x    | x    | o    | x    | o    |
| CTGT | o    | x    | x    | x    | o    | o    | o    |
| CAGT | o    | x    | x    | x    | o    | x    | o    |
| GTTC | x    | o    | o    | o    | x    | x    | x    |
| CATC | o    | x    | o    | x    | x    | x    | x    |
| GATG | o    | o    | o    | o    | x    | x    | x    |

According to another general aspect, there is provided a method of deriving a candidate pair group in which at least three candidates are selected from the general aspect of a candidate group described above to synthesize a nucleic acid nanostructure, the method involving (a') selecting one base sequence to be used from the following Table and screening candidates represented by 'o' in the corresponding base sequence row; (b') selecting another base sequence to be used from pairs of the screened candidates and screening candidates represented by 'o' in the corresponding column; and (c') selecting still another base sequence present in the candidates of all the base sequences selected in steps (a') and (b') to derive a candidate pair group.

TABLE

|      | GAGT | GACT | GTCT | GTGT | GAGA | CTCT | GACA | GTGA |
|------|------|------|------|------|------|------|------|------|
| GAGT | x    | x    | x    | x    | x    | o    | x    | x    |
| GACT | x    | x    | x    | x    | x    | x    | x    | o    |
| GTCT | x    | x    | x    | x    | o    | x    | o    | x    |
| GTGT | x    | x    | x    | x    | x    | x    | o    | x    |
| GAGA | x    | x    | o    | x    | x    | o    | x    | x    |
| CTCT | o    | x    | x    | x    | o    | x    | o    | o    |
| GACA | x    | x    | o    | o    | x    | o    | x    | x    |
| GTGA | x    | o    | x    | x    | x    | o    | x    | x    |
| GTCA | o    | x    | x    | x    | x    | x    | x    | x    |
| CACT | x    | x    | x    | o    | o    | x    | x    | o    |
| CTGT | o    | o    | x    | x    | o    | x    | o    | x    |
| CAGT | x    | x    | o    | x    | o    | x    | o    | o    |
| GTTC | o    | o    | x    | x    | o    | x    | o    | x    |
| CATC | o    | o    | o    | o    | o    | o    | o    | o    |
| GATG | x    | x    | o    | o    | x    | o    | x    | o    |

|      | GTCA | CACT | CTGT | CAGT | GTTC | CATC | GATG |
|------|------|------|------|------|------|------|------|
| GAGT | o    | x    | o    | x    | o    | o    | x    |
| GACT | x    | x    | o    | x    | o    | o    | x    |
| GTCT | x    | x    | x    | o    | x    | o    | o    |
| GTGT | x    | o    | x    | x    | x    | o    | o    |
| GAGA | x    | o    | o    | o    | o    | o    | x    |
| CTCT | x    | x    | x    | x    | x    | o    | o    |
| GACA | x    | x    | o    | o    | o    | o    | x    |
| GTGA | x    | o    | x    | o    | x    | o    | o    |
| GTCA | x    | o    | o    | o    | x    | o    | o    |
| CACT | o    | x    | x    | x    | o    | x    | o    |
| CTGT | o    | x    | x    | x    | o    | o    | o    |
| CAGT | o    | x    | x    | x    | o    | x    | o    |
| GTTC | x    | o    | o    | o    | x    | x    | x    |
| CATC | o    | x    | o    | x    | x    | x    | x    |
| GATG | o    | o    | o    | o    | x    | x    | x    |

According to another general aspect, there is provided a method of synthesizing a dendrimer-like nucleic acid nanostructure using linear nucleic acids comprising the base sequence of 5'-cohesive end prepared by the method described above.

The synthesis may be performed in a ligation buffer comprising a ligation enzyme and a salt.

The synthesis may be performed at a low temperature of 3 to 7° C., room temperature of 16 to 25° C., or a high temperature of 30 to 37° C.

The ligation enzyme may be selected from the group consisting of a T4 ligation enzyme, a *Thermus thermophilus* ligation enzyme, a mammalian DNA ligation enzyme I, a mammalian DNA ligation enzyme II, and a Vaccinia virus DNA ligation enzyme.

The ligation buffer may be under a salt condition in which the salt is present in a concentration of 150 to 200 mM.

The synthesis may be performed at 30 to 37° C. in the ligation buffer having a low salt concentration.

The low salt concentration may be a salt condition in which the salt is present in a concentration of 1 to 50 mM.

In another general aspect, there is provided a dendrimer-like nucleic acid nanostructure synthesized by the general aspect of the method described above, wherein the dendrimer-like nucleic acid nanostructure has an increased synthetic yield and a reduced probability of producing a mismatch ligation product.

In yet another general aspect, there is provided a method of synthesizing a branched nucleic acid nanostructure, the method involving determining a base sequence of 5'-cohesive end of linear nucleic acids by identifying a group of base sequences of 5'-cohesive end having guanine (G)-cytosine (C) content of 50 to 60%, and selecting a candidate group of base sequences based on calculated Gibb's free energy values of each base sequences, and synthesizing a branched nucleic acid nanostructure using a base sequence among the selected candidate group.

The synthesizing of the branched nucleic acid nanostructure may be performed with a ligation enzyme selected from the group consisting of a T4 ligation enzyme, a *Thermus thermophilus* ligation enzyme, a mammalian DNA ligation enzyme I, a mammalian DNA ligation enzyme II, and a Vaccinia virus DNA ligation enzyme.

Other features and aspects may be apparent from the following detailed description, the drawings, and the claims.

BRIEF DESCRIPTION OF THE DRAWINGS

FIG. 1 is a schematic diagram showing (a) examples of Y-shaped nucleic acid structures having a base sequence of 5'-cohesive end, and (b) an example of a dendrimer-like nucleic acid nanostructure having Y-shaped nucleic acid structures synthesized at both sides thereof using a T4 ligation enzyme.

FIG. 2 is a flow chart illustrating an example of a method of determining a thermodynamic or structural candidate group comprising of base sequences of 5'-cohesive end having 4 bases.

FIG. 3 is a schematic diagram illustrating examples of median dendrimer-like nucleic acid nanostructures and base sequences of 5'-cohesive ends of the candidate groups derived in FIG. 2, and thermodynamic information regarding the base sequences.

FIG. 4 is a graph comparing ligation yields experimentally obtained for an example of a candidate group of base sequences of 5'-cohesive end, and a table including yield related information.

FIG. 5 is a graph illustrating ligation yields of a conventional low-purity, low-yield 5'-ohesive end (5'-GCAT) and an example of an expectable high-purity, high-yield 5'-cohesive end (5'-GAGT) according to various temperatures.

FIG. 6A is an image showing electrophoresis results of ligated dendrimer-like nucleic acid nanostructures obtained using various examples of base sequences of 5'-cohesive end having different Gibb's free energy values, and a table comparing total yields of the examples based on the experimental results.

FIG. 6B is a schematic diagram illustrating examples of nucleic acid structures constructed according to the examples illustrated in FIG. 6A.

FIG. 7A is a table illustrating examples of candidate groups having a probability of mismatch ligation.

FIG. 7B is an image showing electrophoresis results indicating that mismatch ligations occur.

FIG. 7C illustrates an example of a method that reduces mismatches in the candidate groups according to FIG. 7A.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

To solve the issues involved in the use of T4 ligation enzymes, the present inventors present candidate groups of base sequences of 5'-cohesive end which are inexpensive and have high purity and yield using theoretical approaches, and a method of selecting the candidate groups of base sequences of 5'-cohesive end. Therefore, the present disclosure has been completed based on these facts.

The present disclosure is directed to a method of preparing a base sequence of 5'-cohesive end of linear nucleic acids to enhance the synthetic yield of a dendrimer-like nucleic acid nanostructure.

Also, the present disclosure is directed to a candidate group consisting of base sequences of 5'-cohesive end of linear nucleic acids prepared by the method in which number of the bases is 4.

Also, the present disclosure is directed to a method of synthesizing a dendrimer-like nucleic acid nanostructure using linear nucleic acids including the base sequence of 5'-cohesive end prepared by the method.

Further, the present disclosure is directed to a dendrimer-like nucleic acid nanostructure synthesized by the synthesis method. Here, the dendrimer-like nucleic acid nanostructure has an increased synthetic yield and a reduced probability of producing a mismatch ligation product.

According to an aspect of the present disclosure, there is provided a method of preparing a base sequence of 5'-cohesive end of linear nucleic acids to enhance the synthetic yield of a nucleic acid nanostructure, may include the following steps:

(a) selecting candidate groups of base sequences of 5'-cohesive end having guanine (G)-cytosine (C) content of 50 to 60%;

(b) calculating Gibb's free energy values of the selected candidate groups of step (a) to select candidates having maximum, median and minimum values, and performing ligation experiments on the candidates;

According to one example of the present disclosure, the candidate group may be selected from the group consisting of GAGT, GACT, GTCT, GTGT, GAGA, CTCT, GACA, GTGA, GTCA, CACT, CTGT, CAGT, CTAG, GATC, GTTC, CATC, and GATG.

According to still another aspect of the present disclosure, there are provided candidate pair groups in the matrix represented by 'o' in the following Table. Here, two candidates are selected from the candidate group, and used to synthesize a nucleic acid nanostructure.

TABLE

|  | GAGT | GACT | GTCT | GTGT | GAGA | CTCT | GACA | GTGA |
|---|---|---|---|---|---|---|---|---|
| GAGT | x | x | x | x | x | o | x | x |
| GACT | x | x | x | x | x | x | x | o |
| GTCT | x | x | x | x | o | x | o | x |
| GTGT | x | x | x | x | x | x | o | x |
| GAGA | x | x | o | x | x | o | x | x |
| CTCT | o | x | x | x | o | x | o | o |
| GACA | x | x | o | o | x | o | x | x |
| GTGA | x | o | x | x | x | o | x | x |
| GTCA | o | x | x | x | x | x | x | x |
| CACT | x | x | x | o | o | x | x | o |
| CTGT | o | o | x | x | o | x | o | x |
| CAGT | x | x | o | x | o | x | o | o |
| GTTC | o | o | x | x | o | x | o | x |
| CATC | o | o | o | o | o | o | o | o |
| GATG | x | x | o | o | x | o | x | o |

|  | GTCA | CACT | CTGT | CAGT | GTTC | CATC | GATG |
|---|---|---|---|---|---|---|---|
| GAGT | o | x | o | x | o | o | x |
| GACT | x | x | o | x | o | o | x |
| GTCT | x | x | x | o | x | o | o |
| GTGT | x | o | x | x | x | o | o |
| GAGA | x | o | o | o | o | o | x |
| CTCT | x | x | x | x | x | o | o |
| GACA | x | x | o | o | o | o | x |
| GTGA | x | o | x | o | x | o | o |
| GTCA | x | o | o | o | x | o | o |
| CACT | o | x | x | x | o | x | o |
| CTGT | o | x | x | x | o | o | o |
| CAGT | o | x | x | x | o | x | o |
| GTTC | x | o | o | o | x | x | x |
| CATC | o | x | o | x | x | x | x |
| GATG | o | o | o | o | x | x | x |

(c) re-selecting the candidate groups having an approximation to the Gibb's free energy values of the candidates which are the most readily ligated based on the experimental results of step (b); and (d) selecting the candidate groups that have a sequence of 3 to 5 different successive bases among the base sequences from the re-selected candidate groups.

According to one example of the present disclosure, the approximation may be in a range of ±0.5 kcal/mol of the Gibb's free energy values of the candidates which are the most readily ligation.

According to another example of the present disclosure, the method may be performed to reduce a probability of producing a mismatch ligation product upon synthesis of a dendrimer-like, X-shaped or T-shaped nucleic acid nanostructure.

According to still another example of the present disclosure, the candidate groups may be groups of base sequences consisting of 4 to 6 bases.

According to another aspect of the present disclosure, there is provided a candidate group consisting of base sequences of 5'-cohesive end of linear nucleic acids prepared by the method in which number of the bases is 4.

According to still another aspect of the present disclosure, there is provided a method of deriving a candidate pair group in which at least three candidates are selected from the candidate group to synthesize a nucleic acid nanostructure, may include the following steps:

(a') first selecting one base sequence to be used from the Table and screening candidates represented by 'o' in the corresponding base sequence row;

(b') selecting another base sequence to be used from pairs of the screened candidates and screening the candidates represented by 'o' in the corresponding column; and (c') selecting still another base sequence present in the candidates of all the base sequences selected in steps (a') and (b') to derive a candidate pair group.

According to still another aspect of the present disclosure, there is provided a method of synthesizing a dendrimer-like nucleic acid nanostructure using linear nucleic acids including the base sequence of 5'-cohesive end prepared by the method.

According to one example of the present disclosure, the synthesis may be performed in a ligation buffer comprising a ligation enzyme, and a salt.

According to another example of the present disclosure, the synthesis may be performed at a low temperature of 3 to 7° C., room temperature of 16 to 25° C., or a high temperature of 30 to 37° C.

According to still another example of the present disclosure, the ligation enzyme may be selected from the group consisting of a T4 ligation enzyme, a *Thermus thermophilus* ligation enzyme, a mammalian DNA ligation enzyme I, a mammalian DNA ligation enzyme II, and a Vaccinia virus DNA ligation enzyme.

According to still another example of the present disclosure, the ligation buffer may be under a salt condition in which the salt is present in a concentration of 150 to 200 mM.

According to still another example of the present disclosure, the salt may be NaCl.

According to still another example of the present disclosure, the synthesis may be performed at 30 to 37° C. in the ligation buffer having a low salt concentration.

According to yet another example of the present disclosure, the low salt concentration may be a salt condition in which the salt is present in a concentration of 1 to 50 mM.

According to yet another aspect of the present disclosure, there is provided a dendrimer-like nucleic acid nanostructure synthesized by the method. Here, the dendrimer-like nucleic acid nanostructure has an increased synthetic yield and a reduced probability of producing a mismatch ligation product.

The present inventors have conducted ardent research to develop a method of reducing mismatch ligations and enhancing the synthetic yield upon synthesis of dendrimer-like nucleic acid structures or X- and T-shaped nucleic acid nanostructures using nucleic acid nanostructures, and to establish an efficient method of preparing a base sequence of 5'-cohesive end of the nucleic acid nanostructure.

Accordingly, the present disclosure may provide a method of preparing a base sequence of 5'-cohesive end of linear nucleic acids to enhance the synthetic yield of a nucleic acid nanostructure, including following steps:

(a) selecting candidate groups of base sequences of 5'-cohesive end having guanine (G)-cytosine (C) content of 50 to 60%;

(b) calculating Gibb's free energy values of the selected candidate groups of step (a) to select candidates having maximum, median and minimum values, and performing ligation experiments on the candidates;

(c) re-selecting the candidate groups having an approximation to the Gibb's free energy values of the candidates which are the most readily ligated based on the experimental results of step (b); and (d) selecting the candidate groups that have a sequence of 3 to 5 different successive bases among the base sequences from the re-selected candidate groups.

The method according to one example of the present disclosure may be used to enhance the yield with which linear nucleic acids including a base sequence of 5'-cohesive end are ligated to synthesize a nucleic acid nanostructure, thereby reducing a probability of producing a mismatch ligation product when the linear nucleic acids are synthesized into a dendrimer-like, X-shaped, or T-shaped nucleic acid nanostructure.

In this regard, the nucleic acid nanostructure having a base sequence of 5'-cohesive end was ligated into a dendrimer-like shape using a T4 ligation enzyme according to one example of the present disclosure. As a result, it was confirmed that the yield of the dendrimer-like nucleic acid nanostructure is different by up to 20 to 25% or more according to the thermodynamic characteristics of the base sequence of 5'-cohesive end. Therefore, the present inventors have provided a theoretical calculation method for finding thermodynamic information on nucleic acid nanostructures having a base sequence of 5'-cohesive end, and found that the expectable high-yield base sequences of 5'-cohesive end of the nucleic acid nanostructures identified by means of the theoretical calculation method have a high synthetic yield at certain Gibb's free energy, and the base sequence of 5'-cohesive end having four bases has an especially high synthetic yield in a Gibb's free energy range of −4.52±0.5 kcal/mol.

Also, according to one example of the present disclosure, new criteria for selecting a candidate group consisting of base sequences of 5'-cohesive end to synthesize an inexpensive high-purity, high-yield nucleic acid nanostructure, arrangement conditions for base sequences, and 5'-cohesive end having a certain Gibb's free energy value according to the criteria and arrangement conditions are provided. In this case, the base sequence of 5'-cohesive end is designed so that the candidate group has GC content of 50% or more so as to unify the conditions associated with the spiral structure (shape) and stability of the nucleic acid nanostructure. Also, the thermodynamic information on the base sequences of 5'-cohesive end which are readily ligated, as experimentally obtained through calculation of the Gibb's free energy values, is calculated to newly re-select the candidate groups satisfying the requirements with which the base sequences of 5'-cohesive end are readily ligated experimentally. To reduce a probability of occurrence of errors in the re-selected candidate groups, three or more successive bases should not be the same in the base sequences of the newly re-selected candidate groups. According to one example of the present disclosure, it is also confirmed that the candidate groups may be derived by the method as described above using base sequences other than the base sequences having a high Gibb's free energy value, such as CG, GC and GG, to obtain the candidate groups having a Gibb's free energy value, which are readily ligated, in the case of the 5'-cohesive ends consisting of four bases. That is, a method of deriving a thermodynamic and structural candidate group for base sequences of 5'-cohesive end consisting of four bases is schematically shown in the flow chart of FIG. 3.

Therefore, in the method according to one example of the present disclosure, steps (b) and (c) may be steps of finding candidates of the base sequence of 5'-cohesive end which are the most readily ligated by means of the experiments, calculating Gibb's free energy values of the candidates and re-selecting the candidate groups having an approximation to the Gibb's free energy values of the candidates. When the number of bases of 5'-cohesive end is 4, the approximation may be preferably in a range of ±0.5 kcal/mol. However, a preferred range of the Gibb's free energy value is deduced from the candidate groups having a base sequence consisting of four bases. In this case, it is apparent to those skilled in the related art that the candidate groups may be deduced by applying the method according to one example of the present disclosure to construction of the base sequences of 5'-cohesive end of the nucleic acid nanostructures consisting of four or more bases in the same manner, and thus the preferred range of the Gibb's free energy value may be set through calculations conducted by those skilled in the related art, but the present disclosure is not limited thereto. However, when the number of bases exceeds 6, the candidate groups may increase exponentially. Therefore, when the candidate groups are established using a group of the base sequences consisting of 4 to 6 bases, only the method according to one example of the present disclosure may be used to deduce the high-yield candidate groups exactly.

Accordingly, the method of synthesizing a nucleic acid nanostructure with high purity and high yield according to one example of the present disclosure (a theoretical calculation method) may be applied to nucleic acid nanostructures as long as the nucleic acid nanostructures have a base sequence of 5'-cohesive end. In this case, the method may be used to obtain the nucleic acid nanostructure with a high yield of at least 90% or more.

Also, the present disclosure may provide a method of synthesizing a dendrimer-like, X-shaped or T-shaped nucleic acid nanostructure using the linear nucleic acids including a base sequence of 5'-cohesive end finally selected in the preparation method, and a candidate group for base sequences of 5'-cohesive end of linear nucleic acids in which number of bases used to enhance the synthetic yield of the nucleic acid nanostructure finally selected in the preparation method is 4.

According to one example of the present disclosure, the candidate group may preferably consist of at least one selected from the group consisting of GAGT, GACT, GTCT, GTGT, GAGA, CTCT, GACA, GTGA, GTCA, CACT, CTGT, CAGT, CTAG, GATC, GTTC, CATC, and GATG. The candidate groups include some of the candidate groups identified according to the experiments conducted to prove the accuracy of the preparation method according to one example of the present disclosure. Therefore, it is apparent that the base sequences of 5'-cohesive end which may be deduced by the preparation method according to one example of the present disclosure may be included in the candidate groups without limitation as long as the mismatch ligation of the base sequences of 5'-cohesive end can be minimized and the base sequences of 5'-cohesive end can be ligated with high yield.

In the present disclosure, experimental information on the probability of mismatch ligation, that is, hybridization between non-complementary base sequences of 5'-cohesive end, and structural hybridization information on the non-complementary base sequences of 5'-cohesive end were presented, and the candidate groups on which mismatch ligations can or cannot be performed were deduced based on the presented information. As a result, it was found that errors may be minimized through the control of the temperature, compared to the candidate groups.

The present inventors determined a synthesis temperature at which it is possible to reduce a probability of mismatch ligations, and also determined the conditions at which errors may be reduced under other salt-concentration conditions, based on previous reports showing that a probability of occurrence of mismatch ligations is reduced under a condition of a ligation buffer having a salt concentration of at least 150 to 200 mM.

The synthesis may be performed in a ligation buffer including a ligation enzyme, and a salt.

According to one example of the present disclosure, it was confirmed that the ligation is performed in the ligation buffer including the ligation enzyme and the salt, and is preferably performed under the ligation temperature conditions including a low temperature of 3 to 7° C., room temperature of 16 to 25° C., or a high temperature of 30 to 37° C. Also, it was confirmed that, when a dendrimer-like DNA nanostructure is synthesized at 30 to 37° C. under a low-salt condition in which the salt is present at a concentration of 1 to 50 mM in the ligation buffer, the dendrimer-like DNA nanostructure may be synthesized with high yield while minimizing a probability of mismatch ligations.

The ligation enzyme may be selected from the group consisting of a T4 ligation enzyme, a *T. thermophilus* ligation enzyme, a mammalian DNA ligation enzyme I, a mammalian DNA ligation enzyme II, and a Vaccinia virus DNA ligation enzyme, but the present disclosure is not limited thereto. For example, since the ligation probability varies according to the ligation enzyme, a ligation enzyme suitable for experimental conditions may be used in consideration of these facts.

Preferred ligation methods for nucleic acid nanostructure-based ligation according to one example of the present disclosure vary according to the thermodynamic state and hybridization structure of cohesive ends, the probability of errors between candidate groups, the synthesis temperature, and the salt concentration, but these parameters may be properly adjusted within a range signified by the theoretical method according to one example of the present disclosure by those skilled in the related art.

Based on the foregoing, the present disclosure may provide a dendrimer-like nucleic acid nanostructure synthesized by the method, characterized in that the nucleic acid nanostructure has an increased synthetic yield and a reduced probability of producing a mismatch ligation product.

Hereinafter, various embodiments are provided to aid in understanding the present disclosure. However, it should be understood that detailed description provided herein is merely intended to provide a better understanding of the present disclosure, and is not intended to limit the scope of the present disclosure.

EXAMPLE 1

Synthesis of Y-shaped Nucleic Acid Structure and Dendrimer-like Nucleic Acid Nanostructure To synthesize a dendrimer-like nucleic acid structure, a body Y-shaped nucleic acid nanostructure was synthesized using three linear nucleic acids $Y_{B1}$, $Y_{B2}$ and $Y_{B3}$ having a complementary hybridization between 13 bases, a left Y-shaped nucleic acid nanostructure was synthesized using $Y_{L1}$, $Y_{L2}$ and $Y_{L3}$, and a right Y-shaped nucleic acid nanostructure was synthesized using $Y_{R1}$, $Y_{R2}$ and $Y_{R3}$.

To synthesize a Y-shaped nucleic acid structure, three linear nucleic acids ($Y_{x1}$, $Y_{x2}$, and $Y_{x3}$) were mixed at a concentration of 6 μM and a ratio of 1:1:1, and annealed for an hour under conditions of 50 mM NaCl, 10 mM Tris-HCl (pH 8.0), and 0.1 mM EDTA solutions. Sequence information on the above-described nucleic acids used is as listed in the following Table 1. In this example, the linear nucleic acids were synthesized by Integrated DNA Technologies.

TABLE 1

| Name | Sequence | SEQ ID NO |
|---|---|---|
| $Y_{B1}$ | 5'/biotin/TGGATCCGCATGACATTCGCC GTAAG-3' | 1 |
| $Y_{B2}$ | 5'/Phosphorylation/GACTCTTACGGC GAATGACCGAATCAGCCT-3' | 2 |
| $Y_{B3}$ | 5'/Phosphorylation/GCATAGGCTGAT TCGGTTCATGCGGATCCA-3' | 3 |
| $Y_{L1}$ | 5'/FAM/TGGATCCGCATGACATTCGCCGTA AG-3' | 4 |

TABLE 1-continued

| Name | Sequence | SEQ ID NO |
|---|---|---|
| $Y_{L2}$ | 5'/FAM/CTTACGGCGAATGACCGAATCAGC CT-3' | 5 |
| $Y_{L3}$ | 5'/Phosphorylation/AGTCAGGCTGAT TCGGTTCATGCGGATCCA-3' | 6 |
| $Y_{R1}$ | 5'/Cy5/TGGATCCGCATGACATTCGCCGTA AG-3' | 7 |
| $Y_{R2}$ | 5'/Cy5/CTTACGGCGAATGACCGAATCAGC CT-3' | 8 |
| $Y_{R3}$ | 5'/Phosphorylation/AGTCAGGCTGAT TCGGTTCATGCGGATCCA-3' | 9 |

The dendrimer-like nucleic acid nanostructure was synthesized by ligating three different Y-shaped nucleic acid structures, and the base sequences of the Y-shaped nucleic acid structures forming the body were ligated using base sequence of 5'-cohesive end of different arts. The body, left, and right Y-shaped nucleic acid structures were added to a concentration of 0.6 µM, and 2 µl of a T4 ligation enzyme and 5 µl of a ligation buffer were then added to prepare 50 µl of a solution. Thereafter, the solution was reacted overnight at 4° C., for 3 hours at 25° C., or for an hour at 37° C. to synthesize a dendrimer-like nucleic acid nanostructure. The synthesis of the dendrimer-like nucleic acid nanostructure was confirmed in an image obtained by performing gel electrophoresis on the reaction solution and staining the reaction solution with ethidium bromide (EtBr).

The base sequence and schematic diagram of the synthesized structure according to Example 1 are shown in FIG. 1.

EXAMPLE 2

Determination of Problems with Base Sequences of 5'-cohesive End and Fluorescent Material for Early Hypothesis Experiment Electrophoresis was performed on the dendrimer-like nucleic acid structure synthesized in Example 1 using the characteristics of a fluorescent material, fluorescein (FAM), which absorbed UV wavelengths to emit fluorescence. In this case, images obtained before and after staining agarose gel with EtBr were compared to determine problems with the cohesive ends of the left and right Y-shaped nucleic acid structures. In this example, it was confirmed that the right cohesive end was problematic. To solve this problem, two experiments were performed.

First, the experiments were performed at different reaction ratios, which are one factor that is important for a chemical reaction. For this purpose, a ligation reaction was performed with an increasing amount of the reaction product of the right Y-shaped nanostructure, and the yields at the reaction ratio of 1:1:1, 1:1:1.2 or 1:1:1.4 for the body, left and right Y-shaped nanostructures were compared, but no increase in the yield was observed.

Next, experiments were performed to determine an effect of concentrations of the Y-shaped nucleic acid nanostructure and the T4 ligation enzyme. For this purpose, an amount of the reaction product was reduced by half while maintaining the concentrations of the T4 ligation enzyme and a ligation buffer. However, no increase in the yield of the dendrimer-like nanostructure was observed.

EXAMPLE 3

Thermodynamic Calculation and Approach of Base Sequences of Cohesive 5'-end

It was confirmed that there were the problems with the physicochemical characteristics of the base sequences of 5'-cohesive end in Example 2, and thus the thermodynamic characteristics of the base sequences of 5'-cohesive end were analyzed. As a result, it was revealed that the left base sequence of 5'-cohesive end had a Gibb's free energy value of −4.52 kcal/mol, and the right base sequence of 5'-ohesive end had a Gibb's free energy value of −6.57 kcal/mol. In this case, the thermodynamic information on the base sequences of 5'-cohesive end was deduced by applying the thermodynamic characteristics between the base sequences to the following Equation and calculating the thermodynamic characteristics ($\Delta g_i$: Helix initiation free energy, and $\Delta g_{sym}$: free energy of a self-complementary sequence or two complementary sequences).

Next, the candidate groups were selected, and Gibb's free energy values ($\Delta G_{Total}$) of the candidate groups were re-verified using an Oligo analyzer program from Integrated DNA Technologies. The $\Delta G°$ values of the two-successive base sequences are listed in the following Table 2 (Proc. Natl. Acad. Sci. USA, 1986, 83, 3746-3750).

$$\Delta G_{Total}=-(\Delta g_i+\Delta g_{sym})+\Sigma_x\Delta G° \qquad \text{Equation:}$$

TABLE 2

| Successive base sequence | $\Delta G°$ (kcal/mol) |
|---|---|
| AA/TT | 1.9 |
| AT/TA | 1.5 |
| TA/AT | 0.9 |
| CA/GT | 1.9 |
| GT/CA | 1.3 |
| CT/GA | 1.6 |
| GA/CT | 1.6 |
| CG/GC | 3.6 |
| GC/CG | 3.1 |
| GG/CC | 3.1 |

Nearest-neighbor thermodynamics. 1 M NaCl, 25° C., pH7

<3-1> Selection Requirements for Base Sequences of 5'-cohesive End and Deduction of Candidate Groups The requirements used to deduce the base sequences of 5'-cohesive end were as described below.

First, for consistency in a spiral structure of the nucleic acid nanostructure, nanostructures having guanine and cytosine content (GC content) of 50 to 60% were designed, and the cohesive ends and the structures themselves having a GC content of 50% were selected as a candidate group. This design requirement serves to restrict A-, B- and Z-type spiral structures of the hybridized DNA nanostructures to the B-type spiral structure. When adenine (A) and thymine (T) are successively arranged, the spiral structures have a probability of forming a Z-type DNA spiral structure due to structural external crushing conditions. Since a base sequence consisting of successive guanine bases forms a tertiary structure consisting of four strands referred to as a G quadruplex, this serves to reduce this probability. Therefore, when it is assumed that the content of the GC bases forming a DNA helix is defined to be maintained at 50 to 60%, the candidate groups of base sequences of 5'-cohesive end may be defined to be $2^4 \times 6$ (=96) rather than $4^4$ (=256).

Second, the Gibb's free energy values of the candidate groups selected thus were calculated to re-select the candidate groups which may be synthesized with high yield. In one example, the candidates having a certain Gibb's free energy value, which are readily ligated, were selected in advance through experiments. For example, the Gibb's free energy values of the cohesive ends consisting of four bases (the highest value to the lowest value for 256 cohesive ends) were in a range of −3.4 to −10.36 kcal/mole. In this example, when the candidate groups were selected according to the first requirement, the candidate groups (the highest value to the lowest value for 96 cohesive ends) had Gibb's free energy values ranging from −3.65 to −7.13 kcal/mole, as listed in the following Table 3. In this example, the criteria for deducing the certain Gibb's free energy values of the candidate groups which were readily ligated were based on the spiral shapes of the cohesive ends. When the Gibb's free energy had a negative (−) value (for example, −7.13 kcal/mole), this meant that the cohesive ends had a strong binding affinity, thereby making it possible to expect the spiral shapes of the cohesive ends to be relatively dense (due to strong biding). Also, when the Gibb's free energy had the smallest negative value (for example, −3.65 kcal/mole), this meant that the cohesive ends had a weak binding affinity, thereby making it possible to expect the spiral shapes of the cohesive ends to be relatively untangled (loose). Based on these criteria, it was experimentally judged which structure (shape) of the cohesive ends would cause the candidate groups to be more readily ligated.

TABLE 3

| Order of hydrogen bond number | 5'- Cohesive end | ΔG (kcal/mol) |
|---|---|---|
| 1. 3322 (binding to #5) | GGAA | −6.59 |
| | GCAA | −7.04 |
| | CGAA | −7.13 |
| | CCAA | −6.97 |
| | GGAT | −6.12 |
| | GCAT | −6.57 |
| | CGAT | −6.66 |
| | CCAT | −6.5 |
| | GGTT | −6.36 |
| | GCTT | −6.68 |
| | CGTT | −6.9 |
| | CCTT | −6.61 |
| | GGTA | −5.37 |
| | GCTA | −5.7 |
| | CGTA | −5.91 |
| | CCTA | −5.63 |
| 2. 3232 (binding to #4) | GAGA | −4.75 |
| | GACA | −4.87 |
| | CAGA | −5.13 |
| | CACA | −5.25 |
| | GAGT | −4.52 |
| | GACT | −4.52 |
| | CAGT | −4.89 |
| | CACT | −4.89 |
| | GTGT | −4.64 |
| | GTCT | −4.52 |
| | CTGT | −4.89 |
| | CTCT | −4.77 |
| | GTGA | −4.87 |

TABLE 3-continued

| Order of hydrogen bond number | 5'- Cohesive end | ΔG (kcal/mol) |
|---|---|---|
| | GTCA | −4.87 |
| | CTGA | −5.13 |
| | CTCA | −5.13 |
| 3. 3223 | GAAG | −5.12 |
| | GAAC | −4.86 |
| | CAAG | −5.5 |
| | CAAC | −5.24 |
| | GATG | −5.0 |
| | GATC | −4.62 |
| | CATG | −5.38 |
| | CATC | −5.0 |
| | GTAG | −3.9 |
| | GTAC | −3.65 |
| | CTAG | −4.16 |
| | CTAC | −3.9 |
| | GTTG | −5.24 |
| | GTTC | −4.86 |
| | CTTG | −5.5 |
| | CTTC | −5.12 |
| 4. 2323 (binding to #2) | AGAG | −4.77 |
| | AGAC | −4.52 |
| | ACAG | −4.89 |
| | ACAC | −4.64 |
| | AGTG | −4.89 |
| | AGTC | −4.52 |
| | ACTG | −4.89 |
| | ACTC | −4.52 |
| | TGAG | −5.13 |
| | TGAC | −4.87 |
| | TCAG | −5.13 |
| | TCAC | −4.87 |
| | TGTG | −5.25 |
| | TGTC | −4.87 |
| | TCTG | −5.13 |
| | TCTC | −4.75 |
| 5. 2233 (binding to #1) | AAGG | −6.61 |
| | AAGC | −6.68 |
| | AACG | −6.9 |
| | AACC | −6.36 |
| | ATGG | −6.5 |
| | ATGC | −6.57 |
| | ATCG | −6.66 |
| | ATCC | −6.12 |
| | TAGG | −5.6 |
| | TAGC | −5.7 |
| | TACG | −5.91 |
| | TACC | −5.37 |
| | TTGG | −6.97 |
| | TTGC | −7.04 |
| | TTCG | −7.13 |
| | TTCC | −6.59 |
| 6. 2332 | AGGA | −6.24 |
| | AGCA | −6.69 |
| | ACGA | −6.53 |
| | ACCA | −6.37 |
| | AGGT | −6.01 |
| | AGCT | −6.34 |
| | ACGT | −6.3 |
| | ACCT | −6.01 |
| | TGGA | −6.6 |
| | TGCA | −7.05 |
| | TCGA | −6.76 |
| | TCCA | −6.6 |
| | TGGT | −6.37 |
| | TGCT | −6.69 |
| | TCGT | −6.53 |
| | TCCT | −6.24 |

That is, a stereochemical aspect was able to be considered based on the Gibb's free energy. Here, the criteria for stereochemical structures with specific spiral shapes were further provided, and included base arrangement and hydrogen bond order. This was derived from the fact that the spiral structures slightly varied according to the base arrangement (successive base components). As listed in the following Table 4, there were four hydrogen bond orders 3-3-2-2, 3-2-3-2, 3-2-2-3, and 2-3-3-2 in the case of a 5'-cohesive end consisting of four bases (since #4 and #5 were bound to #2 and #1, respectively, for the order of base bond number), and the nucleic acid nanostructures optionally had slightly different spiral structures.

TABLE 4

| Order of hydrogen bond number | 5'-Cohesive end | ΔG (kcal/mol) |
|---|---|---|
| 1. 3322 | GGAA | −6.59 |
|  | GCAA | −7.04 |
|  | CGAA | −7.13 |
|  | CCAA | −6.97 |
|  | GGAT | −6.12 |
|  | GCAT | −6.57 |
|  | CGAT | −6.66 |
|  | CCAT | −6.5 |
|  | GGTT | −6.36 |
|  | GCTT | −6.68 |
|  | CGTT | −6.9 |
|  | CCTT | −6.61 |
|  | GGTA | −5.37 |
|  | GCTA | −5.7 |
|  | CGTA | −5.91 |
|  | CCTA | −5.63 |
| 2. 3232 | GAGA | −4.75 |
|  | GACA | −4.87 |
|  | CAGA | −5.13 |
|  | CACA | −5.25 |
|  | GAGT | −4.52 |
|  | GACT | −4.52 |
|  | CAGT | −4.89 |
|  | CACT | −4.89 |
|  | GTGT | −4.64 |
|  | GTCT | −4.52 |
|  | CTGT | −4.89 |
|  | CTCT | −4.77 |
|  | GTGA | −4.87 |
|  | GTCA | −4.87 |
|  | CTGA | −5.13 |
|  | CTCA | −5.13 |
| 3. 3223 | GAAG | −5.12 |
|  | GAAC | −4.86 |
|  | CAAG | −5.5 |
|  | CAAC | −5.24 |
|  | GATG | −5.0 |
|  | GATC | −4.62 |
|  | CATG | −5.38 |
|  | CATC | −5.0 |
|  | GTAG | −3.9 |
|  | GTAC | −3.65 |
|  | CTAG | −4.16 |
|  | CTAC | −3.9 |
|  | GTTG | −5.24 |
|  | GTTC | −4.86 |
|  | CTTG | −5.5 |
|  | CTTC | −5.12 |
| 6. 2332 | AGGA | −6.24 |
|  | AGCA | −6.69 |
|  | ACGA | −6.53 |
|  | ACCA | −6.37 |
|  | AGGT | −6.01 |
|  | AGCT | −6.34 |
|  | ACGT | −6.3 |
|  | ACCT | −6.01 |
|  | TGGA | −6.6 |
|  | TGCA | −7.05 |

TABLE 4-continued

| Order of hydrogen bond number | 5'-Cohesive end | ΔG (kcal/mol) |
|---|---|---|
|  | TCGA | −6.76 |
|  | TCCA | −6.6 |
|  | TGGT | −6.37 |
|  | TGCT | −6.69 |
|  | TCGT | −6.53 |
|  | TCCT | −6.24 |

In summary, experiments were performed using an energy aspect (a Gibb's free energy value) as a major factor and the hydrogen bond order and base arrangement order as minor factors in the second requirement.

A process of preferentially selecting candidates having a certain Gibb's free energy value, which were readily ligated, by the experiments was as described below. For example, in the case of the 5'-cohesive ends consisting of four bases, the candidates having a high energy value (approximately −7.0 kcal/mole, or greater than equal to −10.36 kcal/mole to less than or equal to −7.0 kcal/mole), a median energy value (approximately −5.5 kcal/mole, or more than −7.0 kcal/mole to less than or equal to −5.0 kcal/mole) and a low energy value (approximately −4.0 kcal/mole, or more than −5.0 to less than or equal to −3.0 kcal/mole) were able to be selected and compared, based on the Gibb's free energy. In this Example, candidate groups having a high energy value (5'-GCAA: −7.04 kcal/mole), a median energy value (5'-GCAT: −6.52 kcal/mole), and a low energy value (5'-GACT: −4.52 kcal/mole) were optionally selected, and the ligation yields of the candidate groups were compared. As a result, it was revealed that the candidates for the 5'-cohesive ends having a low energy value (4.52 kcal/mole) were obtained with the highest ligation yield. In the case of the 5'-cohesive ends consisting of four bases, the candidate groups were re-selected, as listed in the following Table 5, using another base arrangement in which another base was present between G and C other than base arrangement having a high energy value, such as CG, GC, and GG, so as to obtain the candidate groups having an energy value corresponding to approximately −4.52 kcal/mol±0.5 kcal/mol.

TABLE 5

| Order of hydrogen bond number | 5'-Cohesive end | ΔG (kcal/mol) |
|---|---|---|
| 2.3232 | GAGA | −4.75 |
|  | GACA | −4.87 |
|  | CAGA | −5.13 |
|  | CACA | −5.25 |
|  | GAGT | −4.52 |
|  | GACT | −4.52 |
|  | CAGT | −4.89 |
|  | CACT | −4.89 |
|  | GTGT | −4.64 |
|  | GTCT | −4.52 |
|  | CTGT | −4.89 |
|  | CTCT | −4.77 |
|  | GTGA | −4.87 |
|  | GTCA | −4.87 |
|  | CTGA | −5.13 |
|  | CTCA | −5.13 |
| 3.3223 | GAAG | −5.12 |
|  | GAAC | −4.86 |

TABLE 5-continued

| Order of hydrogen bond number | 5'-Cohesive end | ΔG (kcal/mol) |
|---|---|---|
| | CAAG | -5.5 |
| | CAAC | -5.24 |
| | GATG | -5.0 |
| | GATC | -4.62 |
| | CATG | -5.38 |
| | CATC | -5.0 |
| | GTAG | -3.9 |
| | GTAC | -3.65 |
| | CTAG | -4.16 |
| | CTAC | -3.9 |
| | GTTG | -5.24 |
| | GTTC | -4.86 |
| | CTTG | -5.5 |
| | CTTC | -5.12 |

Third, in the method of selecting a candidate group having few errors, the requirement was as follows: three or more successive bases of the left and right base sequences of 5'-cohesive end of the Y-shaped nucleic acid structure should be different.

Considering this requirement, the candidate groups were able to be deduced from the flow chart illustrated in FIG. 2. In this case, the experiments were designed in a state in which a repeating sequence such as AGAG was removed as shown in the Venn diagram (repetitive sequence remove), before re-selecting the candidate groups reflecting the third requirement, in consideration of the fact that the repeating sequence had a probability of being present in an undesirable state as will be described below. However, the repeating sequence was considered to have no great influence on the ligation yield, and thus was excluded from the requirements.

<Undesirable State Considered Upon Experiment Design>

```
5' AGAG 3'
    | |
5' TCTC 3'
```

<3-2> Experiments for Determination of Ligation Yield of Candidate Groups

The candidate groups satisfying the requirements of Example <3-1> were selected, and yield comparison experiments were performed on the candidate groups together with a conventional base sequence of 5'-cohesive end (5'-GCAT). The base sequences of the candidate groups and the thermodynamic information on the candidate groups are shown in FIG. 3. After a ligation reaction, the gel electrophoresis results showed that the yields of the base sequences of 5'-cohesive end were different according to the Gibb's free energy. The gel electrophoresis results are shown in the graph and table of FIG. 4. As shown in FIG. 4, it was revealed that the yield of the conventional 5'-GCAT was 65%, and the yield of the newly substituted cohesive end base sequence increased to 83 to 90%.

To summarize the experimental results, it was first revealed that the base sequences of 5'-cohesive end having a certain thermodynamic energy range had a high synthetic yield by the ligation, and second that the base sequence of 5'-cohesive end having the same Gibb's free energy value also had slightly different yields. The results were confirmed to be due to a difference in the stereochemical spiral structures of the base sequences of 5'-cohesive end.

Also, to summarize the complementary sequences in the candidate groups listed in Table 5, the orders of hydrogen bond number, 3232 (12) and 3223 (5), were compressed into high-efficiency cohesive ends, as listed in the following Table 6. In this case, 5' CTAG and 5' GATC of 2. (1) and (2) were used in consideration of the fact that 5' CTAG and 5' GATC had a probability of being self-hybridized.

TABLE 6

| Order of hydrogen bond number | 5'-Cohesive end | | ΔG (kcal/mol) |
|---|---|---|---|
| 1. 3232 | 5' GAGT 3' CTCA | ① | -4.52 |
| | 5' GACT 3' CTGA | ② | -4.52 |
| | 5' GTCT 3' CAGA | ③ | -4.52 |
| | 5' GTGT 3' CACA | ④ | -4.64 |
| | 5' GAGA 3' CTCT | ⑤ | -4.75 |
| | 5' CTCT 3' GAGA | ⑥ | -4.77 |
| | 5' GACA 3' CTGT | ⑦ | -4.87 |
| | 5' GTGA 3' CACT | ⑧ | -4.87 |
| | 5' GTCA 3' CAGT | ⑨ | -4.87 |
| | 5' CACT 3' GTGA | ⑩ | -4.89 |
| | 5' CTGT 3' GACA | ⑪ | -4.89 |
| | 5' CAGT 3' GTCA | ⑫ | -4.89 |
| 2. 3223 | 5' CTAG 3' GATC | (1) | -4.16 |
| | 5' GATC 3' CTAG | (2) | -4.62 |
| | 5' GTTC 3' CAAG | (3) | -4.86 |
| | 5' CATC 3' GTAG | (4) | -5.0 |
| | 5' GATG 3' CTAC | (5) | -5.0 |

EXAMPLE 4

Comparison and Analysis of Ligation Level of Base Sequences of 5'-cohesive End in Y-DNA According to Temperature To determine the ligation yields of the base sequences of 5'-cohesive end under different temperature conditions, an experiment for comparison of ligation yields between the conventional right base sequence of cohesive end, 5'-GCAT, and the right base sequence of cohesive end, 5'-GAGT, having the highest yield was performed. First, the ligation yields were checked at 4° C. (at 0, 60, 120, 240, 320, and 1,380 minutes), and then the ligation yields were checked at 25° C. (at 0, 20, 40, 60, 120, 240, 320, and 1,380 minutes), and 37° C. (at 0, 20, 30, 40, 60, 120, 240, and 320 minutes) to compare the ligation yields according to the temperature.

From the determined results of the ligation yields, it was revealed that the different base sequences of 5'-cohesive end had different ligation yields, but the same base sequences of 5'-cohesive end had no different ligation yields according to the temperature, as shown in FIG. 5.

EXAMPLE 5

Comparison and Analysis of Synthesis Yields of Dendrimer-like Nucleic Acid Nanostructures Since the results showed that the ligation yield of the newly presented right cohesive end increased, experiments were performed to determine to which level the synthesis yields of the dendrimer-like nucleic acid nanostructures increased using the new base sequences of 5'-cohesive end. For this purpose, the left base sequence of 5'-cohesive end was fixed, and the right base sequence of 5'-cohesive end was replaced and ligated.

As a result, it was revealed that the synthesis yields of the dendrimer-like nucleic acid nanostructures using the new base sequences of 5'-cohesive end increased by 10%, as shown in FIG. 6A. The total yield was calculated within an error bound by the following yield equation.

Total Yield Equation=(left ligation probability)×(right ligation probability)

EXAMPLE 6

Evaluation of Probability of Occurrence of Mismatch Ligations

<6-1> Mismatch Ligation Occurrence Experiment and Deduction of Temperature at which Errors are Minimized Experiments were performed to determine a probability of forming mismatch ligations between the base sequences of 5'-cohesive end newly presented according to one example of the present disclosure. First, a theoretical approach for hybridization between non-complementary bases was performed. The probability of possible occurrence of mismatch ligations was able to be determined through the structural correlation between the cohesive ends and the probability of occurrence of mismatch ligations according to a ligation enzyme. In this case, the prior-art document discloses that the mismatch ligations may occur in the case of the T4 ligation enzyme, which is used at a low salt concentration (0 to 50 mM NaCl) at 30 to 37° C., when the cohesive end has a pair of A·C, T·T, T·G, T·C, G·T, C·A, C·T, or A·A (in this case, the pair of A·A was slowly ligated), and that the mismatch ligations are associated with a stereochemical portion when the cohesive end has a spiral structure, based on the results obtained by analyzing hydrogen bonds between bases and resonance structure (Nucleic Acids Research, 1985, 13, 4811-4824). Therefore, the structures in which the mismatch ligations did not occur easily in a structural aspect were predicted to be G·G, C·C, G·A, A·G, and A·A. However, according to one example of the present disclosure, since a mismatch base pair was not present at the end but present inside the base sequence, the mismatch base pair was predicted as a structure having a different influence on double helix structures than the ends. Therefore, the mismatch ligations were included in the possible candidate groups. For comparison, the left and right base sequences of 5'-cohesive end consisting of four bases were compared to determine the candidate groups including three Watson-Crick bonds and a pair of G·G, C·C, T·T, or A·A at the cohesive end. The results are shown in FIG. 7A. The four candidate groups were selected, and the mismatch ligations were confirmed in the candidate groups. As shown in FIG. 7A, it was revealed that both of the (respective) candidate groups having a high ligation yield in the right base sequences of 5'-cohesive end had one left base sequence of 5'-cohesive end, three Watson-Crick base pairs and one mismatch base pair. As a result, the presented candidate groups for the mismatch base pairs were G·G, C·C, T·T, and A·A.

Among these, G·G and C·C were expected to be the structure having a low probability of occurrence of mismatch ligations, and T·T and A·A were expected to be the structure having a high probability of occurrence of mismatch ligations. In the case of the mismatch ligation, it was known that errors were able to be minimized according to the temperature and salt concentration, and the probability of occurrence of mismatch ligations according to the salt concentration was able to reduce errors under a condition of a solution including at least 150 to 200 mM NaCl. Therefore, the present inventors conducted experiments as another approach to determine whether it is possible to reduce the probability of occurrence of mismatch ligations when the salt concentration was fixed at a low salt condition in which NaCl was present at a concentration of 30 to 50 mM, and the ligation temperature was differently set to 25° C. and 37° C. As a result, it was revealed that the T·T and A·A mismatch ligation products were produced at a ligation temperature of 25° C., but no mismatch ligation products were produced at a ligation temperature of 37° C., as shown in FIG. 7B. Accordingly, it was theoretically and experimentally confirmed that, when there was the probability of occurrence of mismatch ligations, the probability of errors was able to be lowered by performing the synthesis at a temperature higher than room temperature or adjusting the salt concentration at a high level.

<6-2> Deduction of Candidate Pair Groups for High-Efficiency Cohesive 5'-Ends Using Experiment for Probability of Occurrence of Mismatch Ligations From the results in Example <6-1>, it was confirmed that errors were able to occur when one identical base pair such as AA or TT which was ligated to be mismatched was present inside the four-base sequences of the cohesive end candidates to be used when the base sequence of 5'-cohesive end consisting of four bases were used. Therefore, a slightly more precise experiment was designed to perform re-experiments on mismatches A, B, C and D of the candidate groups as shown in FIG. 7A. In this example, the probability of occurrence of mismatch pair ligations in non-complementary portions in the presence of complementary cohesive ends was checked in Example <6-1> (that is, it was determined whether the cohesive ends were hybridized with non-complementary arms when the cohesive ends were present in both arms of the Y-shaped nucleic acid structure; it was also determined whether the mismatch pair ligations occurred in the presence of the complementary ends). In this Example, the probability of occurrence of mismatch pair ligations in the non-complementary portions was checked (that is, it was determined whether non-complementary hybridizations occurred when the cohesive end was present in one arm of the Y-shaped nucleic acid structure; it was also determined whether the mismatch pair ligations occurred in the absence of the complementary ends). For this purpose, the conditions in which only the mismatches A, B, C, and D were able to occur were formed, and the probability of occurrence of mismatch pair ligations according to the temperature (4, 25, and 37° C.) was checked. As a result, it was revealed that the mismatch pair ligations occurred in all the mismatches A, B, C, and D (CC, GG, AA, and TT) when the complementary cohesive ends were not present, as shown in FIG. 7C. Thus, it was revealed that the mismatch pair ligations often occurred in GG, AA and TT. Also, it was revealed that the mismatch pair ligations were reduced with an increasing temperature. Therefore, it was confirmed that, when the cohesive end candidates to be used had one different base pair which was not complementary inside the base sequence or was able to cause mismatch pair ligations in the base sequence, the mismatch pair ligations were able to occur.

EXAMPLE 7

Deduction of Candidate Pair Groups when Two or More of Cohesive 5'-end Candidates According to One Example of the Present Disclosure are Used From the results of Example 6, it could be seen that the mismatch pair ligations were possible when two or three bases in the base sequence of 5'-cohesive end consisting of four bases were arranged in such an order. In consideration of this, the candidate pair groups for cohesive ends capable of minimizing the mismatch pair ligations without any change in temperature or salt condition were deduced when two of the candidate groups listed in Table 6 were used (when only one cohesive end was used, it was possible to synthesize a nucleic acid structure using only one of the cohesive ends listed in Table 5). For this purpose, as listed in the following Table 7, first, the candidate groups in which 2 to 3 bases were arranged in the same positions in the cohesive ends listed in Table 6 were marked with "x." Then, the candidate groups in which all the bases were arranged in different positions or one base was arranged in the same position were marked with "○." In summary, when two cohesive ends in the candidate groups for 5'-cohesive ends prepared according to one example of the present disclosure were used, the probability of errors was able to be minimized when the nucleic acid structures having various shapes were intended to be synthesized using the candidate pair groups marked with "○" as listed in the following Table 7, thereby making it possible to synthesize the nucleic acid structures with high efficiency without adjusting the salt and temperature conditions.

TABLE 7

|       | ① | ② | ③ | ④ | ⑤ | ⑥ | ⑦ | ⑧ | ⑨ | ⑩ | ⑪ | ⑫ | (3) | (4) | (5) |
|-------|---|---|---|---|---|---|---|---|---|---|---|---|-----|-----|-----|
| ①     | x | x | x | x | x | ○ | x | x | ○ | x | ○ | x | ○   | ○   | x   |
| ②     | x | x | x | x | x | x | x | ○ | x | x | ○ | x | ○   | ○   | x   |
| ③     | x | x | x | x | ○ | x | ○ | x | x | x | x | ○ | x   | ○   | ○   |
| ④     | x | x | x | x | x | x | ○ | x | x | ○ | x | x | x   | ○   | ○   |
| ⑤     | x | x | ○ | x | x | ○ | x | x | ○ | ○ | ○ | ○ | ○   | ○   | x   |
| ⑥     | ○ | x | x | x | ○ | x | ○ | ○ | x | x | x | x | ○   | ○   | ○   |
| ⑦     | x | x | ○ | ○ | x | ○ | x | x | x | ○ | ○ | ○ | ○   | ○   | x   |
| ⑧     | x | ○ | x | x | x | ○ | x | x | x | ○ | x | ○ | x   | ○   | ○   |
| ⑨     | ○ | x | x | x | x | x | x | x | x | ○ | ○ | ○ | x   | ○   | ○   |
| ⑩     | x | x | x | ○ | ○ | x | x | ○ | ○ | x | x | ○ | x   | x   | ○   |
| ⑪     | ○ | ○ | x | x | ○ | x | ○ | x | ○ | x | x | ○ | ○   | ○   | ○   |
| ⑫     | x | x | ○ | x | ○ | x | ○ | ○ | ○ | x | x | ○ | ○   | x   | ○   |
| (3)   | ○ | ○ | x | x | ○ | x | ○ | x | x | ○ | ○ | ○ | x   | x   | x   |
| (4)   | ○ | ○ | ○ | ○ | ○ | ○ | ○ | ○ | ○ | x | ○ | x | x   | x   | x   |
| (5)   | x | x | ○ | ○ | x | ○ | x | ○ | ○ | ○ | ○ | ○ | x   | x   | x   |

Next, when three of the base sequences of 5'-cohesive end listed in Table 6 were used, the probability of errors was able to be minimized when the nucleic acid structures having various shapes were intended to be synthesized using the candidate pair groups #1 to 33 as listed in the following Table 8, thereby making it possible to synthesize the nucleic acid structures with high efficiency without adjusting the salt and temperature conditions. The candidate pair groups listed in the following Table 8 were deduced using the following sampling process: For example, when the candidate ③ was used as a base sequence of 5'-cohesive end, the candidates ⑤, ⑦, ⑫, (4), and (5) in the row ③ were usable; when the candidate ⑤ was used as another base sequence of 5'-cohesive end among these candidates, the usable candidates were found in the column ⑤. In this case, only the candidates matching the candidate ③ and the usable candidates ⑦, ⑫, (4), and (5) were selected. Therefore, one of the candidate pair groups ③-⑤-⑫ and ③-⑤-(4) was selected and used.

TABLE 8

| No. | Candidate pair group |      |      |
|-----|------|------|------|
| 1   | GAGT | CTCT | CATC |
| 2   | GAGT | GTCA | CTGT |
| 3   | GAGT | GTCA | CATC |
| 4   | GAGT | CTGT | GTTC |
| 5   | GAGT | CTGT | CATC |
| 6   | GACT | GTGA | CATC |

TABLE 8-continued

| No. | Candidate pair group | | |
|---|---|---|---|
| 7 | GACT | CTGT | GTTC |
| 8 | GACT | CTGT | CATC |
| 9 | GTCT | GAGA | CAGT |
| 10 | GTCT | GAGA | CATC |
| 11 | GTCT | GACA | CAGT |
| 12 | GTCT | GACA | CATC |
| 13 | GTCT | GATG | CAGT |
| 14 | GTGT | GACA | CATC |
| 15 | GTGT | CACT | GATG |
| 16 | GAGA | CTCT | CATC |
| 17 | GAGA | CACT | GTTC |
| 18 | GAGA | CTGT | GTTC |
| 19 | GAGA | CTGT | CATC |
| 20 | GAGA | CAGT | GTCT |
| 21 | GAGA | CAGT | GTTC |
| 22 | CTCT | GACA | CATC |
| 23 | CTCT | GTGA | CATC |
| 24 | CTCT | GTGA | GATG |
| 25 | GACA | CTGT | GTTC |
| 26 | GACA | CTGT | CATC |
| 27 | GACA | CAGT | GTTC |
| 28 | GTGA | CACT | GATG |
| 29 | GTGA | CAGT | GATG |
| 30 | GTCA | CACT | GATG |
| 31 | GTCA | CTGT | CATC |
| 32 | GTCA | CTGT | GATG |
| 33 | GTCA | CAGT | GATG |

Even when three or more candidates in the candidate groups for 5'-cohesive ends prepared by the above-described method according to one example of the present disclosure were used, the candidate pair groups were deducible in the same manner as described above.

The present disclosure provides a method of selecting a candidate group for base sequences of 5'-cohesive end to construct a single dendrimer-like nucleic acid structure with low cost, high purity and high yield, and a new experimental and theoretical method of optimizing ligation conditions for reducing mismatch ligations, and thus can be useful in lowering costs by omitting a conventional step of further purifying a reaction product using methods such as HPLC, and maximizing the synthetic yield of the finally synthesized product.

Also, the method according to one example of the present disclosure can be useful in being applicable to nucleic acid structures having different shapes, which can be synthesized using X- and T-shaped nucleic acid nanostructures in addition to the dendrimer-like nucleic acid structure. Further, the method according to one example of the present disclosure can be useful due to its applicability to various ligation enzymes in consideration of the probability of occurrence of mismatch ligations which occur at different frequencies according to the ligation enzyme.

The artificial nucleic acid structures synthesized according to the methods described above may have various utilities, such as nano-medicine, molecular electronics, advanced drug delivery systems, pharmaceutical compounds, biosensors, medical devices and diagnostic devices; however, the utility of the artificial nucleic acid nanostructures are not limited thereto.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of synthesizing a dendrimer-like nucleic acid nanostructure using linear nucleic acids comprising the base sequence of 5'-cohesive end prepared by the method consisting essentially of:
   (a) first, selecting candidate groups of base sequences of 5'-cohesive end having guanine (G)-cytosine (C) content of 50 to 60%;
   (b) second, calculating Gibb's free energy values of the selected candidate groups of the step (a) to select candidates having maximum, median and minimum values, and performing ligation experiments on the candidates;
   (c) third, re-selecting the candidate groups having an approximation to the Gibb's free energy values of the candidates that are the most readily ligated based on the experimental results of step (b); and
   (d) fourth, selecting the candidate groups that have a sequence of 3 to 5 different successive bases among the base sequences from the re-selected candidate groups.

2. The method of claim 1, wherein the synthesis is performed in a ligation buffer comprising a ligation enzyme and a salt.

3. The method of claim 2, wherein the synthesis is performed at a low temperature of 3 to 7 ° C., room temperature of 16 to 25 ° C., or a high temperature of 30 to 37 ° C.

4. The method of claim 2, wherein the ligation enzyme is selected from the group consisting of a T4 ligation enzyme, a Thermus thermophilus ligation enzyme, a mammalian DNA ligation enzyme I, a mammalian DNA ligation enzyme II, and a Vaccinia virus DNA ligation enzyme.

5. The method of claim 2, wherein the ligation buffer is under a salt condition in which the salt is present in a concentration of 150 to 200 mM.

6. The method of claim 2, wherein the synthesis is performed at 30 to 37 ° C. in the ligation buffer having a low salt concentration.

7. The method of claim 6, wherein the low salt concentration is a salt condition in which the salt is present in a concentration of 1 to 50 mM.

8. The method of claim 1, wherein the method is performed to reduce a probability of producing a mismatch ligation product upon synthesis of a dendrimer-like, X-shaped or T-shaped nucleic acid nanostructure.

9. The method of claim 1, wherein a candidate group consisting of base sequences of 5'-cohesive end of linear nucleic acids prepared by the method of claim 7 has a number of the base equal to 4.

10. The method of claim 9, wherein the candidate group is selected from the group consisting of GAGT, GACT, GTCT, GTGT, GAGA, CTCT, GACA, GTGA, GTCA, CACT, CTGT, CAGT, CTAG, GATC, GTTC, CATC, and GATG.

11. The method of claim 10, wherein two candidates comprise a candidate pair group that is represented by 'o' in the following Table, the candidate pair group being used to synthesize a nucleic acid nanostructure:

|      | GAGT | GACT | GTCT | GTGT | GAGA | CTCT | GACA | GTGA |
|------|------|------|------|------|------|------|------|------|
| GAGT | x | x | x | x | x | o | x | x |
| GACT | x | x | x | x | x | x | x | o |
| GTCT | x | x | x | x | o | x | o | x |
| GTGT | x | x | x | x | x | x | o | x |
| GAGA | x | x | o | x | x | o | x | x |
| CTCT | o | x | x | x | o | x | o | o |
| GACA | x | x | o | o | x | o | x | x |
| GTGA | x | o | x | x | x | o | x | x |
| GTCA | o | x | x | x | x | x | x | x |
| CACT | x | x | x | o | o | x | x | o |
| CTGT | o | o | x | x | o | x | o | x |
| CAGT | x | x | o | x | o | x | o | o |
| GTTC | o | o | x | x | o | x | o | x |
| CATC | o | o | o | o | o | o | o | o |
| GATG | x | x | o | o | x | o | x | o |

|      | GTCA | CACT | CTGT | CAGT | GTTC | CATC | GATG |
|------|------|------|------|------|------|------|------|
| GAGT | o | x | o | x | o | o | x |
| GACT | x | x | o | x | o | o | x |
| GTCT | x | x | x | o | x | o | o |
| GTGT | x | o | x | x | x | o | o |
| GAGA | x | o | o | o | o | o | x |
| CTCT | x | x | x | x | x | o | o |
| GACA | x | x | o | o | o | o | x |
| GTGA | x | o | x | o | x | o | o |
| GTCA | x | o | o | o | x | o | o |
| CACT | o | x | x | x | o | x | o |
| CTGT | o | x | x | x | o | o | o |
| CAGT | o | x | x | x | o | x | o |
| GTTC | x | o | o | o | x | x | x |
| CATC | o | x | o | x | x | x | x |
| GATG | o | o | o | o | x | x | x. |

* * * * *